United States Patent [19]
Black et al.

[11] Patent Number: 5,922,742
[45] Date of Patent: Jul. 13, 1999

[54] PYRIDINYL-2-CYCLOPENTEN-1-ONES AS SELECTIVE CYCLOOXYGENASE-2 INHIBITORS

[75] Inventors: Cameron Black, Pointe Claire; Zhaoyin Wang, Pierrefonds; Greg Hughes, Bridgewater, all of Canada

[73] Assignee: Merck Frosst Canada, Kirkland, Canada

[21] Appl. No.: 08/832,407

[22] Filed: Apr. 2, 1997

Related U.S. Application Data

[60] Provisional application No. 60/016,076, Apr. 23, 1996.
[51] Int. Cl.⁶ .......................... A61K 31/44; C07D 211/72
[52] U.S. Cl. .......................... 514/345; 514/277; 546/339; 546/340; 546/301
[58] Field of Search .................... 546/339, 340, 546/290, 286, 318, 304; 514/345, 344, 354, 352, 277

[56] References Cited

U.S. PATENT DOCUMENTS

| | | | |
|---|---|---|---|
| 5,344,991 | 9/1994 | Reitz et al. | 568/34 |
| 5,367,079 | 11/1994 | Bruneau et al. | 546/157 |
| 5,420,287 | 5/1995 | Reitz et al. | 546/339 |
| 5,474,995 | 12/1995 | Durcharme et al. | 514/241 |

FOREIGN PATENT DOCUMENTS

WO 95/00501  1/1995  WIPO.
WO 97/16435  5/1997  WIPO.

*Primary Examiner*—Deborah C. Lambkin
*Attorney, Agent, or Firm*—Richard C. Billups; David L. Rose

[57] ABSTRACT

The invention encompasses the novel compound of Formula I as well as a method of treating COX-2 mediated diseases comprising administration to a patient in need of such treatment of a non-toxic therapeutically effective amount of a compound of Formula I.

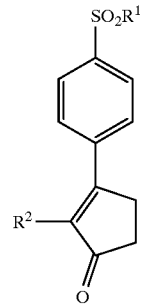

I

The invention also encompasses certain pharmaceutical compositions for treatment of COX-2 mediated diseases comprising compounds of Formula I.

13 Claims, No Drawings

PYRIDINYL-2-CYCLOPENTEN-1-ONES AS SELECTIVE CYCLOOXYGENASE-2 INHIBITORS

Provisional application No. 60/016,076 filed Apr. 23, 1996.

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX-1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for the treatment of glaucoma.

The potential utilities of selective cyclooxygenase-2 inhibitors are discussed in the following articles:

1. John Vane, "Towards a better aspirin" in *Nature*, Vol. 367, pp. 215–216, 1994
2. Bruno Battistini, Regina Botting and Y. S. Bakhle, "COX-1 and COX-2: Toward the Development of More Selective NSAIDs" in *Drug News and Perspectives*, Vol. 7, pp. 501–512, 1994.
3. David B. Reitz and Karen Seibert, "Selective Cyclooxygenase Inhibitors" in *Annual Reports in Medicinal Chemistry*. James A. Bristol, Editor, Vol. 30, pp. 179–188, 1995.

U.S. Pat. No. 5,474,995 (Dec. 12, 1995) and World Patent Application 95/00501 (Jan. 5, 1995) disclose compounds represented by Formula A as being useful in the treatment of COX-2 mediated diseases, by virtue of their selective inhibition of COX-2 rather than COX-1. We have now discovered that a subset of the compounds represented by A, in which —X—Y—Z— is —C(O)CH$_2$CH$_2$-and R$^2$ is pyridinyl or substituted pyridinyl show unexpectedly superior selectivity for the inhibition of COX-2 over COX-1 and/or superior potency as compared to the closest species disclosed in 95/00501. This subset of compounds is the subject of the present invention and is represented by Formula I.

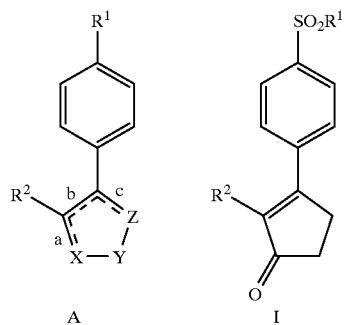

Of the 150-plus specific compounds disclosed in U.S. Pat. No. 5,474,995 and World Patent Application 95/00501 only 10 of them are cyclopentenones, and none of these latter is a pyridinyl cyclopentenone. Furthermore, among the variety of specific compounds disclosed, only one of them contains a heterocyclic group in the place of R$^2$, and that group is quinoline, not pyridine.

SUMMARY OF THE INVENTION

The invention encompasses the novel compound of Formula I as well as a method of treating COX-2 mediated diseases comprising administration to a patient in need of such treatment of a non-toxic therapeutically effective amount of a compound of Formula I.

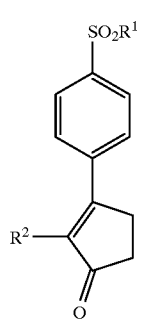

The invention also encompasses certain pharmaceutical compositions for treatment of COX-2 mediated diseases comprising compounds of Formula I.

DETAILED DESCRIPTION OF THE INVENTION

The invention encompasses the novel compound of Formula I as well as a method of treating COX-2 mediated diseases comprising administration to a patient in need of such treatment of a non-toxic therapeutically effective amount of a compound of Formula I

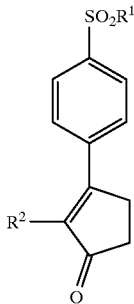

I wherein:
R$^1$ is selected from the group consisting of
(a) CH$_3$,
(b) NH$_2$,
(c) NHC(O)CF$_3$,
(d) NHCH$_3$;
R$^2$ is a mono-, di-, or tri-substituted pyridinyl, wherein the substituents are chosen from the group consisting of
(a) hydrogen,
(b) halo,
(c) C$_{1-6}$alkoxy,
(d) C$_{1-6}$alkylthio,
(e) CN,
(f) C$_{1-6}$alkyl,
(g) C$_{1-6}$fluoroalkyl,
(h) N$_3$,
(i) —COOR$^3$,
(j) hydroxy,
(k) —C(R$^3$)(R$^4$)—OH,
(l) —C$_{1-6}$alkyl-CO$_2$-R$^3$,
(m) C$_{1-6}$fluoroalkoxy;
R$^3$ and R$^4$ are independently chosen from the group consisting of
(a) hydrogen,
(b) C$_{1-6}$alkyl,
or R$^3$ and R$^4$ together with the carbon to which they are attached form a saturated monocyclic carbon ring of 3, 4, 5, 6 or 7 atoms.

A preferred sub-generic structure of compound I is that wherein R$^2$ is a mono-, di-, or trisubstituted 2-pyridinyl, and the remainder of the substituents are as described for I.

Another preferred sub-generic structure of compound I is that wherein R$^2$ is a mono-, di-, or trisubstituted 3-pyridinyl, and the remainder of the substituents are as described for I.

Yet another preferred embodiment of structure I is that wherein R$_1$ is CH$_3$ or NH$_2$.

Another preferred embodiment of structure I is that wherein the substituents on R$^2$ are chosen from the group consisting of
(a) hydrogen,
(b) halo,
(c) C$_{1-6}$alkoxy,
(d) C$_{1-6}$alkylthio,
(e) C$_{1-6}$alkyl,
(f) CF$_3$,
(g) CN.

The following abbreviations have the indicated meanings:
AA=arachidonic acid
Ac=acetyl
AIBN=2.2--azobisisobutyronitrile
BHT=butylated hydroxytoluene
Bn=benzyl
dba=dibenzylideneacetone
DMAP=4-(dimethylamino)pyridine
DMF=N,N-dimethylformamide
DMSO=dimethyl sulfoxide
EDTA=ethylenediaminetetraacetic acid
Et$_3$N=triethylamine
HBSS=Hanks balanced salt solution
HEPES=N-[2-Hydroxyethyl]piperazine-N$^1$-[2-ethanesulfonic acid]
HWB=human whole blood
KHMDS=potassium hexamethyldisilazane
LDA=lithium diisopropylamide
LPS =lipopolysaccharide
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
NMP=N-methylpyrrolidone
NSAID=non-steroidal anti-inflammatory drug
PCC=pyridinium chlorochromate
PDC=pyridinium dichromate
PEG=polyethyleneglycol
Ph=phenyl
r.t.=room temperature
rac.=racemic
Tf=trifluoromethanesulfonyl=triflyl
TfO=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl
SO$_2$Me=methyl sulfone
SO$_2$NH$_2$=sulfonamide
Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl
Dose Abbreviations
bid=bis in die=twice daily qid=quater in die=four times a day tid=ter in die=three times a day For purposes of this specification alkyl is defined to include linear, branched and cyclic stuctures, with the indicated number of carbon atoms. Examples of alkyl are methyl, ethyl, propyl, s- and t-butyl, butyl, pentyl, hexyl, 1,1-dimethylethyl, cyclopropyl, cyclobutyl, cyclohexylmethyl and the like. Similarly, alkoxy and alkylthio mean linear, branched and cyclic stuctures, with the indicated number of carbon atoms.

For purposes of this specification fluoroalkyl means alkyl groups of the indicated number of carbon atoms in which one hydrogen or more is replaced by fluorine. Examples are —$CF_3$, —$CH_2CH_2F$, —$CH_2CF_3$, c-Pr-$F_5$, c-Hex-$F_{11}$ and the like. Similarly, fluoroalkoxy means linear, branched and cyclic stuctures, with the indicated number of carbon atoms.

For purposes of this specification, in situations in which a term occurs two or more times, the definition of the term in each occurrence is independent of the definition in each additional occurrence.

For purposes of this specification halo means F, Cl, Br, or I.

In another embodiment, the invention encompasses pharmaceutical compositions for inhibiting COX-2 and for treating COX-2 mediated diseases as disclosed herein comprising a pharmaceutically acceptable carrier and non-toxic therapeutically effective amount of a compound of formula I as described above.

In yet another embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

Optical Isomers—Diastereomers—Geometric Isomers

Some of the compounds described herein contain one or more asymmetric centres and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N--dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, hydrabamine, N-(2-hydroxyethyl) piperidine, N-(2-hydroxyethyl)pyrrolidine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment which follows, references to the compounds of Formula I are meant to also include the pharmaceutically acceptable salts.

Utilities

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumour growth and hence can be used in the treatment of cancer. Compound 1 may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease, for decreasing bone loss particularly in postmenopausal women (i.e. treatment of osteoporosis) and for treatment of glaucoma.

By virtue of its high inhibitory activity against COX-2 and/or its specificity for COX-2 over COX-1, compound I will prove useful as an alternative to conventional NSAID'S, particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

Pharmaceutical Compositions

For the treatment of any of these cyclooxygenase mediated diseases compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, benzyl alcohol, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dose Ranges

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

Similarly, compound of Formula I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetaminophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a prostaglandin including misoprostol, enprostil, rioprostil, ornoprostol or rosaprostol: a diuretic; a sedating or non-sedating antihistamine. In addition the invention encompasses a method of treating cyclooxygenase mediated diseases comprising: administration to a patient in need of such treatment a non-toxic therapeutically effective amount of the compound of Formula I, optionally co-administered with one or more of such ingredients as listed immediately above.

Methods of Synthesis

The compounds of the present invention can be prepared according to the following methods.

Method A

Cyclopentenone (II) may be halogenated with bromine or iodine followed by treatment with a base to give III (see Organic Syntheses 61 65). An appropriately substituted pyridine boronic acid may then be added via a palladium-catalyzed coupling reaction to form IV. 4-Bromothioanisole may be metalated with nBuLi or magnesium, and then treated with IV to give the alcohol V. Oxidation with allylic transposition may then be accomplished using an oxidant such as PDC to give cyclopentenone VI. Sulfide oxidation using an oxidant such as MMPP or mCPBA then provides sulfone Ia. Alternatively, VI may be converted to sulfonamide Ib as described in U.S. Pat. No. 5,474,995.

Method A:

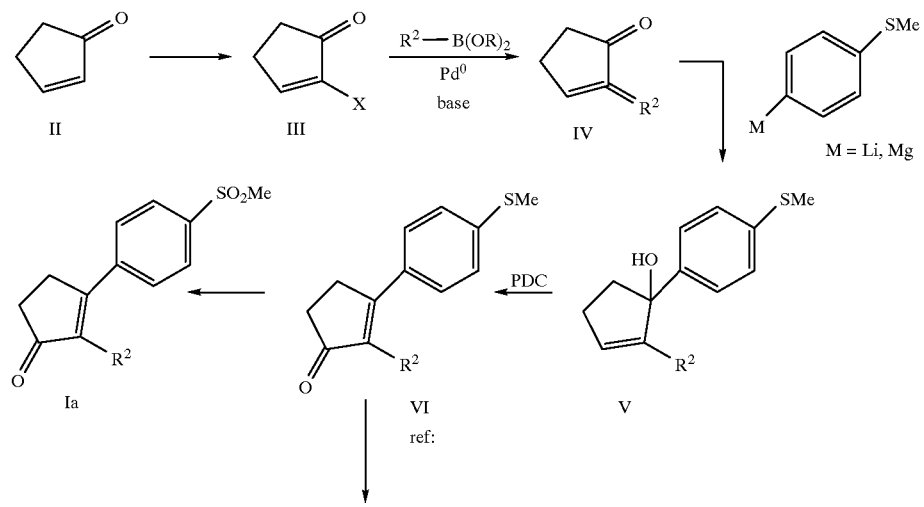

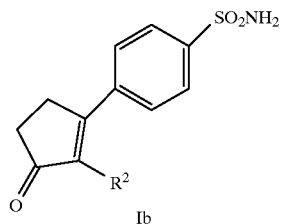

Method B

To bromocyclopentenone IIIa is added lithio or magnesium thioaiiisole to give tertiary alcohol VII. Oxidation with a reagent such as PDC then provides the ketone VIII. The sulfide may be oxidized at this point using an oxidant such as MMPP or mCPBA to give the sulfone IX. Palladium-catalyzed coupling of an appropriately substituted pyridinyl boronic acid then provides Ia.

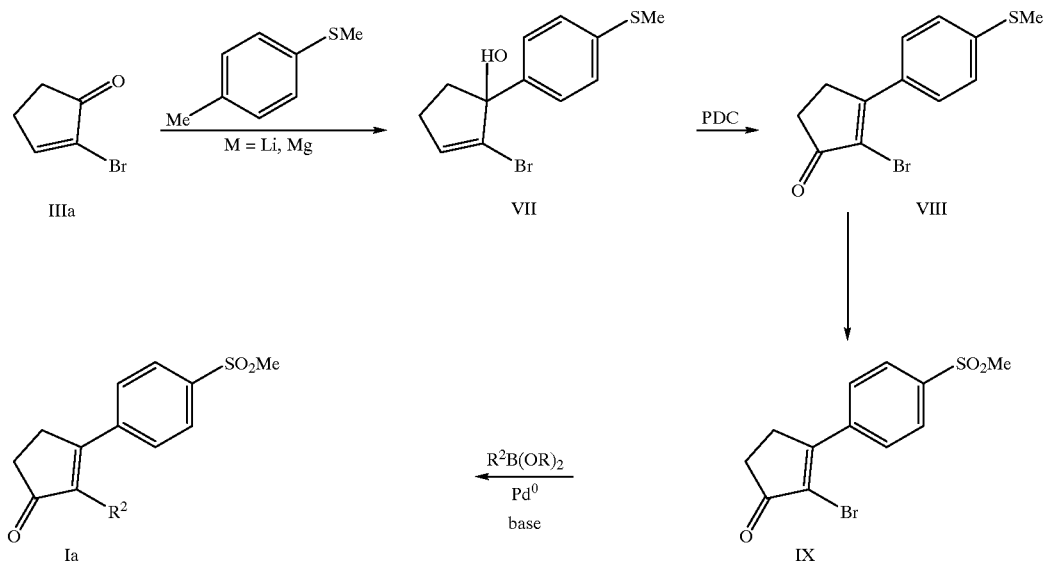

Method C

An appropriately substituted methylpyridine X may be deprotonated with an alkyl lithium reagent and the resulting anion added to a diamide XI to provide the ketoamide XII. Cyclization of this intermediate with a base such as DBU provides the enol XIII which can then be converted to the triflate XIV. A palladium-catalyzed coupling reaction with 4-(methylthio)phenylboronic acid in the presence of an appropriate base then provides sulfide VI which can be oxidized to give the sulfone Ia or the sulfonamide Ib as described in Method A.

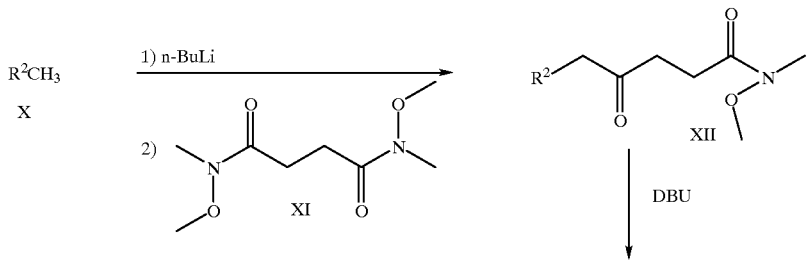

-continued
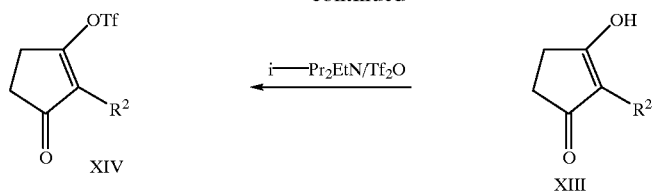
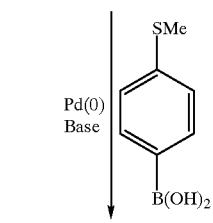
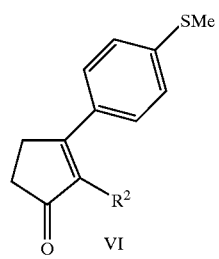
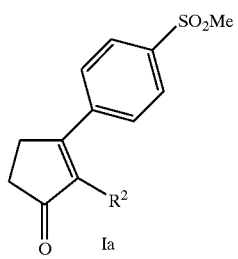
Representative Compounds
Table I illustrates compounds of formula I, which are representative of the present invention.
TABLE I
| | EXAMPLE |
|---|---|
| 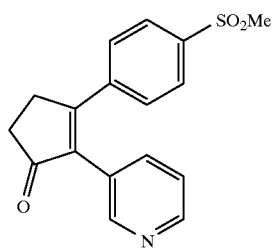 | 1 |
| 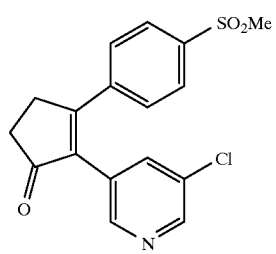 | 2 |
TABLE I-continued
| | EXAMPLE |
|---|---|
| 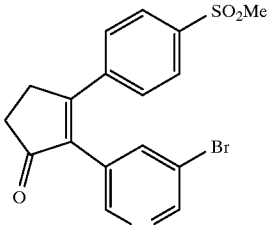 | 3 |
| 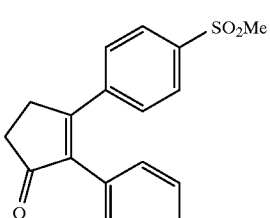 | 4 |
| 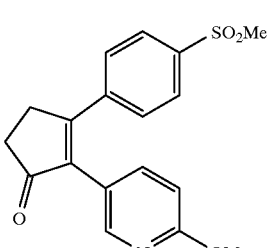 | 5 |

TABLE I-continued
| | EXAMPLE |
|---|---|
| 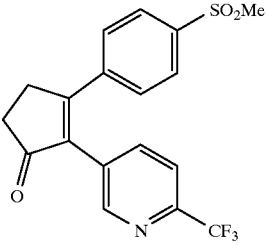 | 6 |
| 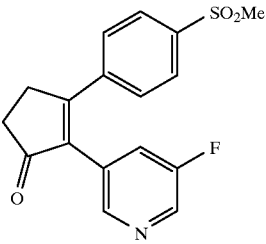 | 7 |
| 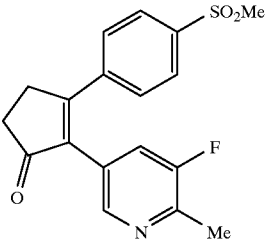 | 8 |
| 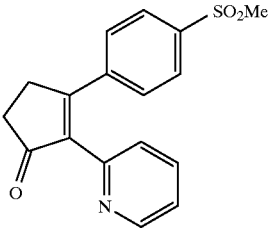 | 9 |
| 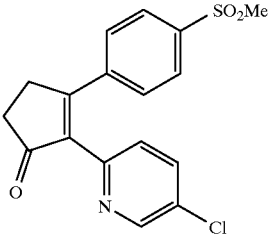 | 10 |
| 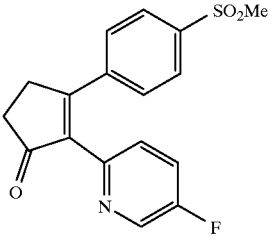 | 11 |
TABLE I-continued
| | EXAMPLE |
|---|---|
| 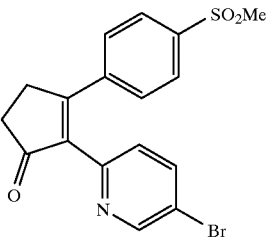 | 12 |
| 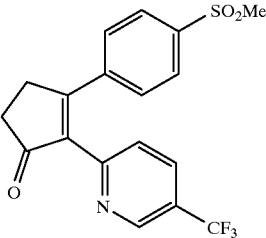 | 13 |
| 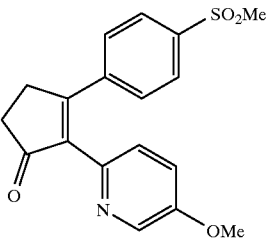 | 14 |
| 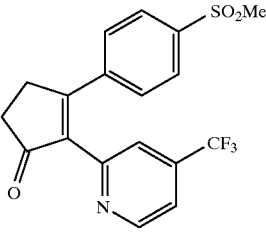 | 15 |
| 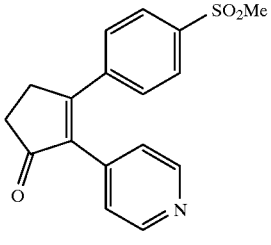 | 16 |
| 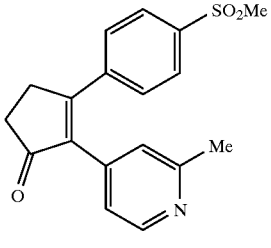 | 17 |

TABLE I-continued

| | EXAMPLE |
|---|---|
| 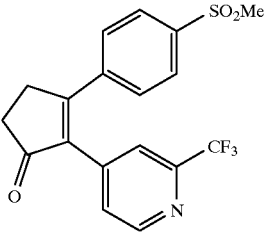 | 18 |

Assays for Determining Biological Activity

The compound of Formula I can be tested using the following assays to determine their COX-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to AA, using a radioimmunoassay. Cells used for these assays are human osteosarcoma 143 cells (which specifically express COX-2) and human U-937 cells (which specifically express COX-1). In these assays, 100% activity is defined as the difference between prostaglandin $E_2$ synthesis in the absence and presence of arachidonate.

Whole Cell Assays

For cyclooxygenase assays, osteosarcoma cells are cultured in 1 mL of media in 24-well multidishes (Nunclon) until confluent (1–2 ×10$^5$ cells/well). U-937 cells are grown in spinner flasks and resuspended to a final density of 1.5×10$^6$ cells/mL in 24well multidishes (Nunclon). Following washing and resuspension of osteosarcoma and U-937 cells in 1 mL of HBSS, 1 μL of a DMSO solution of test compound or DMSO vehicle is added, and samples gently mixed. All assays are performed in triplicate. Samples are then incubated for 5 or 15 minutes at 37° C., prior to the addition of AA. AA (peroxide-free, Cayman Chemical) is prepared as a 10 mM stock solution in ethanol and further diluted 10-fold in HBSS. An aliquot of 10 μL of this diluted solution is added to the cells to give a final AA concentration of 10 μM. Control samples are incubated with ethanol vehicle instead of AA. Samples are again gently mixed and incubated for a further 10 min. at 37° C. For osteosarcoma cells, reactions are then stopped by the addition of 100 μL of 1N HCl, with mixing and by the rapid removal of the solution from cell monolayers. For U-937 cells, reactions are stopped by the addition of 100 μL of 1N HCl, with mixing. Samples are then neutralized by the addition of 100 μL of 1N NaOH and PGE$_2$ levels measured by radioimmunoassay.

Whole Cell Assays for COX-2 and COX-1 using CHO Transfected Cell Lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of 1.5×10$^6$ cells/ml. Drugs to be tested are dissolved in DMSO to 66.7-fold the highest test drug concentration. Compounds are typically tested at 8 concentrations in duplicate using serial 3-fold serial dilutions in DMSO of the highest drug concentration. Cells (0.3×10$^6$ cells in 200 μl) are preincubated with 3 μl of the test drug or DMSO vehicle for 15 min at 37° C. Working solutions of peroxide-free AA (5.5 μM and 110 μM AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 μM AA in the CHO[hCOX-1] assay and a final concentration of 10 μM AA in the CHO[hCOX-2] assay. The reaction is terminated by the addition of 10 μl 1N HCl followed by neutralization with 20 μl of 0.5N NaOH. The samples are centrifuged at 300×g at 4° C. for 10 min, and an aliquot of the clarified supernatant is appropriately diluted for the determination of PGE$_2$ levels using an enzyme-linked immunoassay for PGE$_2$ (Correlate PGE$_2$ enzyme immunoassay kit, Assay Designs, Inc.). Cyclooxygenase activity in the absence of test compounds is determined as the difference in PGE$_2$ levels of cells challenged with AA versus the PGE$_2$ levels in cells mock-challenged with ethanol vehicle. Inhibition of PGE$_2$ synthesis by test compounds is calculated as a percentage of the activity in the presence of drug versus the activity in the positive control samples.

Assay of COX-1 Activity from U937 cell microsomes

U 937 cells are pelleted by centrifugation at 500×g for 5 min and washed once with phosphate-buffered saline and repelleted. Cells are resuspended in homogenization buffer consisting of 0.1M Tris-HCl, pH 7.4, 10 mM EDTA, 2 μg/ml leupeptin, 2 μg/ml soybean trypsin inhibitor, 2 μg/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 μg/ml in 0.1M Tris-HCl buffer, pH 7.4 containing 10 mM EDTA, 0.5 mM phenol, 1 mM reduced glutathione and 1 μM hematin. Assays are performed in duplicate in a final volume of 250 μl. Initially, 5 μl of DMSO vehicle or drug in DMSO are added to 20 μl of 0.1M Tris-HCl buffer, pH 7.4 containing 10 mM EDTA in wells of a 96-deepwell polypropylene titre plate. 200 μl of the microsomal preparation are then added and preincubated for 15 min at room temperature before addition of 25 μl of 1M arachidonic acid in 0.1M Tris-HCl and 10 mM EDTA, pH 7.4. Samples are incubated for 40 min at room temperature and the reaction is stopped by the addition of 25 μl of 1N HCl. Samples are neutralized with 25 μl of 1N NaOH prior to quantitation of PGE$_2$ content by radioimmunoassay (Dupont-NEN or Amersham assay kits). Cyclooxygenase activity is defined as the difference between PGE$_2$ levels in samples incubated in the presence of arachidonic acid and ethanol vehicle.

Assay of the Activity of Purified Human COX-2

The enzyme activity is measured using a chromogenic assay based on the oxidation of N,N,N',N'-tetramethyl-p-phenylenediamine (TMPD) during the reduction of PGG$_2$ to PGH$_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin, 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM AA and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D./min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on PGE2 production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2 mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2μL of vehicle (DMSO) or 2 μL of a test compound at final concentrations varying from 10 mM to 30μM for 24 hours at 37° C. At the end of the incubation, the blood is centrifuged at 12,000×g for 5 minutes to obtain plasma. A 100μL aliquot of plasma is mixed with 400 μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX-1 (Clotting-induced $TxB_2$ production)

Fresh blood is collected into vacutainers containing no anticoagulants. Aliquots of 500μL are immediately transferred to siliconized microcentrifuge tubes preloaded with 2μL of either DMSO or a test compound at final concentrations varying from 10 nM to 30μM. The tubes are vortexed and incubated at 37° C. for 1 hour to allow blood to clot. At the end of incubation, serum is obtained by centrifugation (12,000×g for 5 min.). A 100μL aliquot of serum is mixed with 400μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 μt of 1% carrageenan solution in saline (FMC Corp, Maine) into the paw using an insulin syringe with a 25-gauge needle (i.e. 500 μg carrageenan per paw). Three hr later, the paw volume (V3) is measured and the increases in paw volume ($V_3-V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of COX-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{51}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400μ Ci of sodium $^{51}$chromate for 30 min. at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20μ Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ ($5\mu$ Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

PHARMACOKINETICS IN RATS

Per Os Pharmacokinetics in Rats

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3"gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15min, 30min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

PEG 200/300/400: restricted to 2 mL/kg

Methocel 0.5% –1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

Intravenous Pharmacokinetics in Rats

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15min, 30min, 1h, 2 h, 6 h or 0, 5 min, 30min, 1 h, 2 h, 4 h, 6 h.

Vehicles:

The following vehicles may be used in IV rat blood level determinations:

Dextrose: 1 mL/kg

Moleculosol 25%: 1 mL/kg

DMSO (dimethylsulfoxide): Restricted to a dose volume of 0.1 mL per animal

PEG 200: Not more than 60% mixed with 40% sterile water–1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h·kg (milliliters per hour kilogram)

Representative Biological Data

Compounds of the present invention are inhibitors of COX-2 and are thereby useful in the treatment of COX-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of AA, COX-1 or COX-2 and a putative inhibitor. The $IC_{50}$ values represent the concentration of putative inhibitor required to lower PGE$_2$ synthesis to 50% of that obtained as compared to the uninhibited control.

Data from three of these biological assays is given for representative compounds in Table II, along with comparative data for the following three compounds from U.S. Pat. No. 5,474,995:

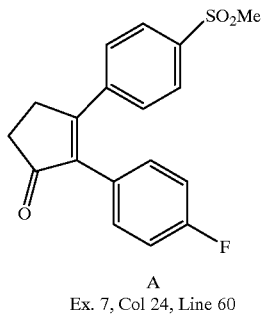

A
Ex. 7, Col 24, Line 60

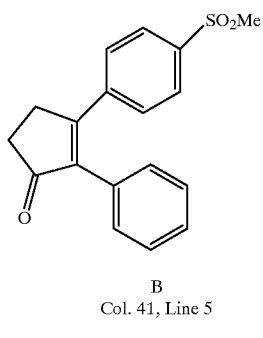

B
Col. 41, Line 5

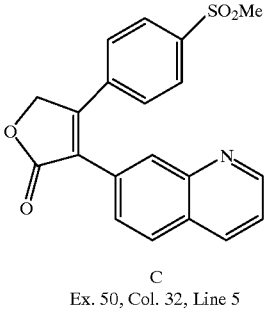

C
Ex. 50, Col. 32, Line 5

TABLE II

| Example | Cox-2 Whole Blood (IC$_{50}$, μM) | Cox-1 U937 (IC$_{50}$, μM) | Selectivity Ratio | Rat Paw Edema (ED$_{50}$, mg/kg) |
| --- | --- | --- | --- | --- |
| A | 0.09 | 0.45 | 5 | 3.0 |
| B | 0.19 | 1.9 | 10 | 10 |
| C | 0.59 | 0.6 | 1 | — |
| 1 | 0.58 | 30 | 52 | 1.7 |
| 2 | 0.89 | >100 | >112 | — |
| 10 | 0.46 | 36 | 78 | 2.5 |

As can be seen from this data, the compounds of the present invention show greater COX-2 selectivity and/or potency than A, B, and C. The basicity of the pyridine ring in these examples also permits the formation of acid salts, resulting in increased water solubility and give the potential for parenteral administration in aqueous vehicles.

The invention will now be illustrated by the following non-limiting examples in which, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and d' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300MHz or 400MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)), r.t. (room temperature).

EXAMPLE 1

3-(4-(Methylsulfonyl)phenyl)-2-(3-pyridinyl)-2-cyclopenten-1-one

Step 1: 2-Bromo-2-cyclopenten-1-one

To a 0° C. solution of 2-cyclopenten-1-one (125 g, 1.52 mol) in CCl$_4$ (1.2 L) in a three-neck flask equipped with an overhead stirrer was added a solution of bromine (269 g, 1.68 mol) in CCl$_4$ (400 mL) dropwise over 4 h, maintaining an internal temperature <2° C. A solution of Et$_3$N (310 mL, 2.22 mol) in CCl$_4$ (200 mL) was then added dropwise over 1.5 h, maintaining an internal temperature <10° C. The resulting suspension was warmed to r.t. for 1 h, then cooled to 0° C. and filtered. The filtrate was washed with two 700 mL portions of 3M HCl and 500 mL of brine, then filtered through cotton. Concentration provided 228 g of an orange oil which was crystalized from 150 mL of 2:1 hexane: ether to provide 191 g of the title compound.

$^1$H NMR (CD$_3$COCD$_3$) δ 7.94 (1H, t), 2.72 (2H, m), 2.46 (2H, m).

Step 2: 2-Bromo-3-(4-(methylthio)phenyl)-2-cyclopenten-1-one

To a –78° C. solution of 4-bromothioanisole (35.1 g, 173 mmol) in THF (500 mL) was added nBuLi (1.6M in hexanes, 107.5 mL, 172 mmol). The solution was stirred for 45 min, then a solution of 2-bromo-2-cyclopenten-1-one (25.4 g, 158 mmol) in THF (150 mL) was added and the mixture was allowed to warm to 0° C. and was quenched with saturated aqueous NH$_4$Cl. The majority of the solvent was removed in vacuo and the residue was suspended in water and extracted with two portions of EtOAc. The organic layers were washed with brine, dried over MgSO$_4$, filtered and concentrated. This material was dissolved in DMF (300 mL), cooled to 0° C. and treated with PDC (72.4 g, 192 mmol). The resulting mixture was warmed to r.t. and stirred for 2 h, then poured into H$_2$O (1.2 L) and extracted with two 500 mL portions of EtOAc. The organic layers were washed with brine, dried over MgSO$_4$, filtered and concentrated to give the title compound as a light brown solid which was used directly in the next step.

Step 3: 2-Bromo-3-(4-(methylsulfonyl)phenyl)-2-cyclopenten-1-one

To a 0° C. solution of 2-bromo-3-(4-(thiomethyl)phenyl)-2-cyclopenten-1-one in 2:1 CH$_2$Cl$_2$/MeOH (500 mL) was added MMPP (100 g). The mixture was stirred at r.t. overnight, then concentrated and partitioned between saturated NaHCO$_3$, 1M Na$_2$S$_2$O$_3$ and CH$_2$Cl$_2$. The aqueous layer was extracted with CH$_2$Cl$_2$, and the combined organics were washed with brine, filtered through cotton and evaporated. The resulting solid was swished in CH$_2$Cl$_2$/Et$_2$O to provide 23 g of the title compound.

$^1$H NMR (CD$_3$COCD$_3$) δ 8.12 (4H, m), 3.22 (2H, m), 3.20 (3H, s), 2.69 (2H, m).

Step 4: Lithium 3-pyridinyltrimethyl boronate

To a –88° C. solution of 3-bromopyridine (10.1 1 mL, 104.8 mmol) in Et$_2$O (450 mL) was added a 1.6M hexane solution of n-BuLi (66 nL, 105.6 mmol). The reaction mixture was warmed to –78° C. for 1 h to give a thick yellow slurry. Triisopropyl borate (26 ml, 112.7 mmol) was then added to give a slight exotherm (–78° C. to –63° C.) and a clear solution. The mixture was stirred at –78° C. for 15 min, then warmed to r.t. and concentrated to dryness. The residue was dissolved in MeOH and concentrated three times to give 27.2 g of pyridin-3-yl-trimethyl lithium boronate. This material was used in the next step without further purification.

$^1$H NMR (CD$_3$OD, 400MHz) δ 7.15 (1H, m), 7.85 (1H, h), 8.15 (1H, m), 8.50 (1H, m)

Step 5: 3-(4-(Methylsulfonyl)phenyl)-2-(3-pyridinyl)-2-cyclopenten-1-one

To a mixture of 2-bromo-3-(4-(methylsulfonyl)phenyl)-2-cyclopenten-1-one (3.37 g, 10.7 mmol), lithium 3-pyridinyltrimethyl boronate (3.43 g, 18.2 mmol), Pd$_2$(dba)$_3$ (0.196 g, 0.214 mmol), and PPh$_3$ (0.224 g, 0.855 mmol) was added toluene (75 m) L), n-propanol (25 nL), and H$_2$O (25 mL). The mixture was degassed and stirred under N$_2$ for 15 min then heated to reflux. After 4 h, the reaction mixture was cooled to r.t., diluted with 100 mL of CH$_2$Cl$_2$ and washed with H$_2$O. The aqueous layer was separated and washed 3 times with 100 mL of CH$_2$Cl$_2$. The organic layers were combined, washed with brine and filtered through cotton. The filtrate was concentrated to dryness and the residue was purified by flash chromatography (100% EtOAc) followed by swishing in a mixture of CH$_2$Cl$_2$ and Et$_2$O to provide 2.6 g of the title compound.

$^1$H NMR (CDCl$_3$) δ 8.55 (1H, m), 8.34 (1H, m), 7.40 (2H, m), 7.65 (1H, m), 7.49 (2H, m), 7.33 (1H, m), 3.12 (2H, m), 3.05 (3H, s), 2.80 (2H, m).

Step 6: 3-(4-(Methylsulfonyl)phenyl)-2-(3-pyridinyl)-2-cyclopenten-1-one hydrochloride To a solution of 3-(4-(methylsulfonyl)phenyl)-2-(3-pyridinyl)-2-cyclopenten-1-one (5.0 g, 15.96 mmol) in CH$_2$Cl$_2$ (50 mL) was passed a stream of HCl gas for 10 min. Excess HCl was removed by bubbling a stream of air through the solution. The solution was then concentrated and swished in Et$_2$O to give 5.7 g of the title compound.

$^1$H NMR (CDCl$_{13}$) δ 8.70 (1H, m), 8.52 (1H, m), 8.38 (1H, m), 8.00 (2H, m), 7.94 (1H, m), 7.50 (2H, m), 3.20 (2H, m), 3.13 (3H, s), 2.85 (2H, m). ps Step 7: 3-(4-(Methylsulfonyl)phenyl)-2-(3-pyridinyl)-2-cyclopenten-1-one hydromethanesulfonate To a solution of 3-(4-(methylsulfonyl)phenyl)-2-(3-pyridinyl)-2-cyclopenten-1-one (104 mg, 0.33 mmol) in CH$_2$Cl$_2$ (50 mL) was added methanesulfonic acid (0.02 mL, 0.32 mmol) and the solution was concentrated to give a foam. The foam was swished in Et$_2$O to give 108 mg of the title compound as an off-white solid.

EXAMPLE 2

2-(5-Chloropyridin-3-yl)-3-(4-(methylsulfonyl) phenyl)-2-cyclopenten-1-one

Step 1: Trifluoromethanesulfonic acid 5-chloro-3-pyridinyl ester

To a –78° C. solution of 5-chloro-3-hyroxypyridine (1.0 g, 7.72 mmol) and diisopropylethyl amine (1.88 mL, 10.81 mmol) in CH$_2$Cl$_2$ (35 mL) was added trifluoromethanesulfonic anhydride (1.55 mL, 9.26 mmol) slowly to give a dark red solution. After 1 mL of trifluoromethanesulfonic anhydride was added, a precipitate formed and the mixture became hard to stir. The mixture was immersed in a –10° C. bath and the rest of the trifuoromethanesulfonic anhydride was added. After 15 min, the mixture was washed with H$_2$O and brine, filtered through cotton and concentrated to dryness. The residue was purified by flash chromatography (10% EtOAc/hexanes) to give 510 mg of the title compound.

$^1$H NMR (CD$_3$COCD$_3$) δ 8.75 (2H, m), 8.20 (1H, m).

Step 2: 3-Trimethylstannanyl-5-chloropyridine

To a mixture of Pd$_2$(dba)$_3$ (0.038 g, 0.04 mmol) and PPh$_3$ (0.086 g, 0.33 mmol) was added dioxane (2 nL). The resulting suspension was degassed and stirred at r.t. for fifteen minutes before it was transferred via cannula into a degassed r.t. mixture of trifluoromethanesulfonic acid 5-chloro-3-pyridinyl ester (0.510 g, 2.06 mmol), hexamethylditin (0.443 mL, 2.16 mmol), LiCl (0.262 g, 6.18 mmol), and a few crystals of BHT. The resulting mixture was heated to reflux for 2.5 h, then cooled to r.t., diluted with EtOAc, washed with 10% NH$_4$OH and brine, dried over MgSO$_4$, filtered, and concentrated to dryness. The residue was used in step 3 without further purification.

Step 3: 2-(5-Chloro-3-pyridinyl)-3-(4-(methylsulfonyl) phenyl)-2-cyclopenten-1-one To a degassed r.t. solution of 2-bromo-3-(4-(methylsulfonyl)phenyl)-2-cyclopenten-1-one (0.630 g, 2.0 mmol), Pd$_2$(dba)$_3$ (0.037 g, 0.04 mmol), and AsPh$_3$ (0.098 g, 0.32 mmol) in 5 mL NMP was added a degassed NMP solution (5 mL) of 3-trimethylstannanyl-5-chloropyridine (~2.0 mmol). The resulting mixture was heated to 60° C. for 16 h. The mixture was then cooled to r.t., diluted with EtOAc, washed with water and brine, dried over MgSO$_4$, and concentrated to dryness. The residue was purified by flash chromatography (80% EtOAc/hexanes) followed by a CH$_2$Cl$_2$/Et$_2$O swish to provide 0.215 g of the title compound.

$^1$H NMR (CD$_3$COCD$_3$) δ 8.50 (1H, d), 8.20 (1H, d), 7.95 (2H, m), 7.22, (1H, dd), 7.18 (2H, m), 3.22 (2H, m), 3.16 (3H, s), 2.71 (2H, m).

EXAMPLE 3

2-(5-Bromo-3-pyridinyl)-3-(4-(methylsulfonyl) phenyl)-2-cyclopenten-1-one

Step 1: Lithium 5-bromo-3-pyridinyltrimethyl boronate

To a –105° C. solution of 3,5-dibromopyridine (2.00 mL, 8.44 mmol) in Et$_2$O (40 mL) was added a 1.6M solution of n-BuLi (5.54 mL, 8.86 mmol). The reaction mixture was allowed to stir at −105° C. for five minutes to give a yellow precipitate. Triisopropyl borate (3.90 mL, 16.88 mmol) was then added and the reaction mixture was allowed to warm to r.t. The residue was diluted with MeOH and concentrated three times to give a white solid which was used in the next step without further purification.

Step 2: 2-(3-Pyridinyl)-3-(4-(methylsulfonyl)phenyl)-2-cyclopenten-1-one

To a mixture of 2-bromo-3-(4-(methylsulfonyl)phenyl)-2-cyclopenten-1-one (0.500 g, 1.59 mmol), lithium 5-bromo-3-pyridinyltrimethyl boronate (0.729 g, 3.17 mmol), $Pd_2(dba)_3$ (0.044 g, 0.048 mmol), and $PPh_3$ (0.050 g, 0.190 mmol) was added toluene (15 mL), n-propanol (5 mL), and $H_2O$ (5 mL). The mixture was degassed and stirred under $N_2$ for 15 min before diethyl amine (0.427 mL, 4.12 mmol) was added and the mixture was heated to reflux. After three hours, the reaction mixture was cooled to r.t., diluted with $CH_2Cl_2$ and washed with $H_2O$. The $H_2O$ was separated and washed 3 times with $CH_2Cl_2$. The organic layers were combined, washed with brine and filtered through cotton. The filtrate was concentrated to dryness and the residue was purified by flash chromatography (75% ETOAc/hexanes) followed by a $CH_2Cl_2/Et_2O$ swish, to yield 0.160 g of the title compound.

$^1$H NMR ($CD_3COCD_3$) δ 8.60 (1H, d), 8.25 (1H, d), 7.96 (2H, m), 7.37 (1H, dd), 7.69 (2H, m), 3.22 (2H, m), 3.14 (3H, s), 2.73 (2H, m).

EXAMPLE 4

2-(2-Methyl-5-pyridinyl)-3-(4-(methylsulfonyl) phenyl)-2-cyclopenten-1-one

Step 1: Trifluoromethanesulfonic acid 2-methyl-5-pyridinyl ester

To a −78° C. solution of 2-methyl-5-hydroxypyridine (1.0 g, 9.16 mmol) and diisopropylethyl amine (2.23 mL, 12.83 mmol) in $CH_2Cl_2$ (50 mL) was added trifluoromethanesulfonic anhydride (1.85 mL, 11.0 mmol). The reaction mixture was then allowed to warm to r.t. After 30 min, the mixture was washed with water and brine, filtered through cotton and concentrated to dryness. The residue was purified by flash chromatography (12.5% EtOAc/hexanes) to give 0.483 g of the title compound.

$^1$H NMR ($CD_3COCD_3$) δ 8.57 (1H, d), 7.80 (1H, dd), 7.47 (1H, d), 2.55 (3H, s).

Step 2: 5-Trimethylstannanyl-2-methylpyridine

To a mixture of $Pd_2(dba)_3$ (0.047 g, 0.04 mmol), and $PPh_3$ (0.085 g, 0.32 mnmol) was added dioxane (2 mL). The resulting suspension was degassed and stirred at r.t. for 15 min before it was transferred via cannula into a degassed r.t. dioxane suspension (8 mL) of trifluoromethanesulfonic acid 2-methyl-5-pyridinyl ester (0.460 g, 2.02 mmol), hexamethylditin (0.435 mL, 2.13 mmol), LiCl (0.257 g, 6.07 mmol), and a few crystals of BHT. The resulting mixture was heated to reflux for 2.5 h before it was cooled to r.t., diluted with $CH_2Cl_2$, washed with 10% NH40H and brine, filtered through cotton, and concentrated to dryness. The residue was used in step 3 without further purification.

Step 3: 2-(2-Methyl-5-pyridinyl)-3-(4-(methylsulfonyl) phenyl)-2-cyclopenten-1-one To a degassed r.t. solution of 2-bromo-3-(4-(methylsulfonyl)-phenyl)-2-cyclopenten-1-one (0.315 g, 1.0 mmol), $Pd_2(dba)_3$ (0.018 g, 0.02 mmol), and $AsPh_3$ (0.049 g, 0.16 mmol) in NMP (2.5 mL) was added a degassed NMP solution (2.5 mL) of 5-trimethylstannanyl-2-methylpyridine (~2.0 mmol). The resulting mixture was heated to 60° C. for 16 hours, then to 100° C. for a further 3.5 h. The mixture was then cooled to r.t., diluted with EtOAc, washed 2 times with 10% $NH_4OH$ and brine, dried over $MgSO_4$, and concentrated to dryness. The residue was purified by flash chromatography (100% EtOAc/hexanes) to provide 0.070 g of the title compound as a rigid foam.

$^1$H NMR ($CD_3COCD_3$) δ 8.20 (1H, d), 7.94 (2H, m), 7.65 (2H, m), 7.47 (1H, dd), 7.20 (1H, d), 3.18 (2H, m), 3.14 (3H, s), 2.69 (2H, m).

EXAMPLE 5

2-(2-Methoxy-5-pyridinyl)-3-(4-(methylsulfonyl) phenyl)-2-cyclopenten-1-one

Step 1: 5-Bromo-2-methoxypyridine

To a solution of 2,5-dibromopyridine (1.4 g, 5.9 mmol) in DMF (10 mL) was added MeOH (4 mL), and 8N aqueous KOH (1 mL). The solution was heated to 100° C. for 2 h, then cooled and partitioned between $Et_2O$ and $H_2O$. The organic layer was washed with brine, dried over $MgSO_4$ and concentrated to provide 840 mg of the title compound, which was used in the next step without further purification.

Step 2: Lithium 2-methoxy-5-pyridinyltrimethyl boronate

To a −78° C. solution of the total sample of 5-bromo-2-methoxypyridine from Step 1 in $Et_2O$ (20 mL) was added a 1.6M solution of n-BuLi (3.5 mL, 5.6 mmol). The reaction mixture was allowed to stir 10 min to give an orange suspension. Triisopropyl borate (1.5 mL, 6.5 mmol) was then added and the reaction mixture was allowed to warm to r.t. The residue was diluted with MeOH and concentrated three times to give a white solid which was used in the next step without further purification.

Step 3: 2-(2-Methoxy-5-pyridinyl)-3-(4-(methylsulfonyl) phenyl)-2-cyclopenten-1-one A mixture of the total sample of lithium 2-methoxy-5-pyridinyltrimethyl boronate from Step 2, 2-bromo-3-(4-(methylsulfonyl)phenyl)-2-cyclopenten-1-one (400 mg, 1.3 mmol), $Pd_2(dba)_3$ (70 mg, 0.08 mmol) and $PPh_3$ (83 mg, 0.32 mmol) was dissolved in 3:1:1 toluene: n-propanol: $H_2O$ (50 mL) and degassed. The solution was stirred 10 min at r.t., heated to reflux for 2.5 h, then cooled and concentrated in vacuo. The residue was partitioned between $CH_2Cl_2$ and aqueous $NaHCO_3$. The organic phase was washed with brine, filtered through cotton and concentrated. Purification by flash chromatography (60% EtOAc/hexanes) provided 317 mg of an oil which was crystalized from EtOAc/hexanes to give 230 mg of the title compound.

$^1$H NMR ($CD_3COCD_3$, 300MHz) δ 7.95 (3H, m); 7.68 (2H, m); 7.48 (1H, dd); 6.72 (1H, dd), 3.87 (3H, s), 3.14 (2H, m), 3.12 (3H, s), 2.68 (2H, m).

EXAMPLE 9

2-(2-Pyridinyl)-3-(4-(methylsulfonyl)phenyl)-2-cyclopenten-1-one

Step 1: Trifluoromethanesulfonic acid 2-pyridinyl ester

To a −78° C. solution of 2-hydroxypyridine (1.0 g, 10.5 mmol) and diisopropylethyl amine (2.56 mL, 14.7 mmol) in $CH_2Cl_2$ (40 mL) was added trifluoromethanesulfonic anhydride (2.12 mL, 12.6 mmol). The reaction mixture was then allowed to warm to r.t. After 25 min, the mixture was washed with $H_2O$ and brine, filtered through cotton and concentrated to dryness. The residue was purified by flash chromatography (9% EtOAc/hexanes) to give 1.60 g of the title compound.

$^1$H NMR ($CD_3COCD_3$) δ 8.46 (1H, m), 8.18 (1H, m), 7.62 (1H, m), 7.49 (1H, d).

Step 2: 2-Trimethylstannanyl pyridine

To a mixture of $Pd_2(dba)_3$ (0.129 g, 0.14 mmol), and $PPh_3$ (0.296 g, 1.13 mmol) was added dioxane (6 mL). The resulting suspension was degassed and stirred at r.t. for 15 min before it was transferred via cannula into a degassed r.t. suspension of triuoromethanesulfonic acid 2-pyridinyl ester (1.6 g, 7.04 mmol), hexamethylditin (1.51 mL), 7.40 mmol), LiCl (0.895 g, 21.1 mmol), and a few crystals of BHT in dioxane (23 mL). The resulting mixture was heated to reflux for 3 h before it was cooled to room temperature, diluted with $CH_2Cl_2$, washed with 10% $NH_4OH$ and brine, filtered through cotton, and concentrated to dryness. The residue was used in step 3 without further purification.

Step 3: 2-(2-Pyridinyl)-3-(4-(methylsulfonyl)phenyl)-2-cyclopenten-1-one

To a degassed r.t. solution of 2-bromo-3-(4-(methylsulfonyl)phenyl)-2-cyclopenten-1-one (1.103 g, 3.5 mmol), $Pd_2(dba)_3$ (0.064 g, 0.07 mmol), and $AsPh_3$ (0.171 g, 0.56 mmol) in NMP (7.5 mL) was added a degassed NMP solution (10 mL) of 2-trimethylstannanyl pyridine (~7.0 mmol). The resulting mixture was heated to 100° C. for 16 hours. The mixture was then cooled to r.t., diluted with EtOAc, washed 3 times with 10% $NH_4OH$ and brine, dried over $MgSO_4$, and concentrated to dryness. The residue was purified by flash chromatography (5% MeOM/EtOAc) to provide 0.215 g of the title compound.

$^1$H NMR ($CD_3COCD_3$) δ 8.46 (1H, m), 7.88 (2H, m), 7.80 (1H, m), 7.62 (2H, m), 7.45 (1H, m), 7.30 (1H, m), 3.21 (2H, m), 3.12 (2H, m), 2.71 (2H, m).

EXAMPLE 10

2-(5-Chloro-2-pyridinyl)-3-(4-(methylsulfonyl) phenyl)-2-cyclopenten-1-one

Step 1: Trifluoromethanesulfonic acid 5-chloro-2-pyridinyl ester

To a −78° C. solution of 5-chloro-2-hydroxypyridine (1.0 g, 7.72 mmol) and diisopropylethyl amine (1.88 mL, 10.81 mmol) in $CH_2Cl_2$ (35 mL) was added trifluoromethanesulfonic anhydride (1.56 mL, 9.26 mmol), and the reaction mixture was allowed to warm to r.t. After 30 min, the mixture was washed with $H_2O$ and brine, filtered through cotton and concentrated to dryness. The residue was purified by flash chromatography (8% EtOAc/hexanes) and to give 1.0 g of the title compound.

$^1$H NMR ($CD_3COCD_3$) δ 8.50 (1H, d), 8.23 (1H, dd), 7.58 (1H, d).

Step 2: 2-Trimethylstannanyl-5-chloropyridine

To a degassed room temperature mixture of trifluoromethanesulfonic acid 5-chloro-3-pyridinyl ester (0.510 g, 2.06 mmol), hexamethylditin (0.443 mL, 2.16 mmol), LiCl (0.262 g, 6.18 mmol), and a few crystals of BHT were added a freshly prepared solution of 0.1M solution of $Pd(PPh_3)_4$ in toluene (0.807 mL, 0.081 mmol). The resulting mixture was heated to reflux for 1.5 h before it was cooled to r.t., diluted with EtOAc, washed with 10% $NH_4OH$ and brine, dried over $MgSO_4$, filtered, and concentrated to dryness. The residue was used in step 3 without further purification.

Step 3: 2-(5-Chloro-2-pyridinyl)-3-(4-(methylsulfonyl) phenyl)-2-cyclopenten-1-one To a degassed r.t. solution of 2-bromo-3-(4-(methylsulfonyl)-phenyl)-2-cyclopenten-1-one (0.630 g, 2.0 mmol), $Pd_2(dba)_3$ (0.036 g, 0.04 mmol), and $AsPh_3$ (0.098 g, 0.32 mmol) in NMP (5 mL) was added a degassed NMP solution (8 mL) of 2-trimethylstannanyl-5-chloropyridine (~4.0 mmol). The resulting mixture was heated to 60° C. for 16 h, then to 100° C. for a further 2 h. The mixture was then cooled to r.t., diluted with EtOAc, washed 2 times with 10% $NH_4OH$ and brine, dried over $MgSO_4$, and concentrated to dryness. The residue was purified by flash chromatography (70% EtOAc/hexanes) followed by a $CH_2Cl_2/Et_2O$ swish to provide 130 mg of the title compound.

$^1$H NMR ($CD_3SOCD_3$) δ 8.54 (1H, d), 8.00 (1H, dd), 7.39 (2H, m), 7.55 (2H, m), 7.45 (1H, d), 3.23 (3H, s), 3.13 (2H, m), 2.69 (2H, m).

EXAMPLE 12

2-(5-Bromo-2-pyridinyl)-3-(4-(methylsulfonyl) phenyl)-2-cyclopenten-1-one

Step 1: 2-Trimethylstannanyl-5-bromopyridine

A mixture of 2,5-dibromopyridine (1.42 g, 6.0 mmol), $Pd_2(dba)_3$ (178 mg, 0.19 mmol) and $PPh_3$ (315 mg, 1.20 mmol) was dissolved in dioxane (15 mL) and degassed. After 10 min at r.t., hexamethylditin (1.4 mL, 6.8 mmol) was added and the mixture was heated to reflux for 1.5 h, then cooled to r.t. The mixture was partitioned between saturated aqueous $NaHCO_3$ and $CH_2Cl_{12}$. The organic phase was washed with brine, filtered through cotton and concentrated. The residue was used directly in step 2 without further purification.

Step 2: 2-(5-Bromo-2-pyridinyl)-3-(4-(methylsulfonyl) phenyl)-2-cyclopenten-1-one A mixture of 2-bromo-3-(4-(methylsulfonyl)-phenyl)-2-cyclopenten-1-one (700 mg, 2.2 mmol), $Pd_2(dba)_3$ (170 mg, 0.18 mmol), and the total sample of 2-trimethylstannanyl-5-bromopyridine from Step 1 was dissolved in NMP (10 mL) and degassed. The resulting solution was heated to 100° C. for 3.5 h then cooled. The mixture was diluted with EtOAc, washed 2 times with 10% $NH_4OH$ and brine, dried over $MgSO_4$, and concentrated. The residue was purified by flash chromatography (70% EtOAc/hexanes) followed by an EtOAc/$Et_2O$ swish to provide 110 mg of the title compound.

$^1$H NMR ($CDCl_3$, 300MHz) δ 8.59 (1H, d), 7.90 (3H, m), 7.48 (2H, m), 7.40 (1H, d), 3.12 (2H, m), 3.06 (3H, s), 2.80 (2H, m).

EXAMPLE 16

2-(4-Pyridinyl)-3-(4-(methylsulfonyl)phenyl)-2-cyclopenten-1-one

Step 1: Lithium 4-pyridinyltrimethyl boronate

To a −107° C. solution of 4-bromopyridine (1.77 g, 11.20 mmol) in $Et_2O$ (50 mL) was added a 1.6M solution of n-BuLi(5.54 mL, 8.86 mmol). The reaction mixture was allowed to stir at −105° C. for five minutes. Triisopropyl borate (3.62 mL, 15.68 mmol) was then added and the reaction mixture was then allowed to warm to r.t. The reaction mixture was diluted with MeOH and concentrated three times to give a white solid which was used in the next step without further purification.

$^1$H NMR ($CD_3OD$, 400MHz) δ8.19 (2H, m), 7.47 (2H, m)

Step 2: 2-(4-Pyridinyl)-3-(4-(methylsulfonyl)phenyl)-2-cyclopenten-1-one

To a mixture of 2-bromo-3-(4-(methylsulfonyl)phenyl)-2-cyclopenten-1-one (0.500 g, 1.59 mmol), lithium 4-pyridinyltrimethyl boronate (0.480 g, 2.54 mmol), $Pd_2(dba)_3$ (0.029 g, 0.03 mmol), and $PPh_3$ (0.033 g, 0.13 mmol) was added toluene (15 mL), n-propanol (5 mL), and $H_2O$ (5 mL). The mixture was degassed and stirred under $N_2$ for 15 min before it was heated to reflux. After 3.5 h, the reaction mixture was cooled to r.t., diluted with $CH_2Cl_2$, washed with $H_2O$ and brine, and filtered through cotton. The filtrate was concentrated to dryness and the residue was purified by flash chromatography (5% MeOH/EtOAc) followed by a $CH_2Cl_2/Et_2O$ swish, to yield 0.130 g of the title product.

$^1$H NMR ($CD_3COCD_3$) δ 8.53 (2H, m), 7.95 (2H, m), 7.63 (2H, m), 7.15 (2H, m), 3.20 (2H, m), 3.14 (3H, s), 2.71 (2H, m).

What is claimed is:
1. A compound of Formula I

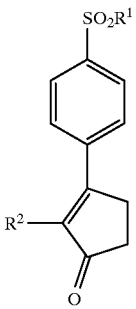

or a pharmaceutically salt thereof wherein:
$R^1$ is selected from the group consisting of
(a) $CH_3$,
(b) $NH_2$,
(c) $NHC(O)CF_3$,
(d) $NHCH_3$;
$R^2$ is a mono-, di-, or tri-substituted pyridinyl, wherein the substituents are chosen from the group consisting of
(a) hydrogen,
(b) halo,
(c) $C_{1-6}$alkoxy,
(d) $C_{1-6}$alkylthio,
(e) CN,
(f) $C_{1-6}$alkyl,
(g) $C_{1-6}$fluoroalkyl,
(h) $N_3$,
(i) —$COOR^3$,
(j) hydroxy,
(k) —$C(R^3)(R^4)$—OH,
(l) —$C_{1-6}$alkyl-$CO_{2-R^3}$,
(m) $C_{1-6}$fluoroalkoxy;
$R^3$ and $R^4$ are independently chosen from the group consisting of
(a) hydrogen,
(b) $C_{1-6}$alkyl,
or $R^3$ and $R^4$ together with the carbon to which they are attached form a saturated monocyclic carbon ring of 3, 4, 5, 6 or 7 atoms.

2. A compound according to claim 1 wherein $R^2$ is a mono-, di-, or trisubstituted 2-pyridinyl.

3. A compound according to claim 1 wherein $R^2$ is a mono-, di-, or trisubstituted 3-pyridinyl.

4. A compound according to claim 1 wherein $R^1$ is $CH_3$ or $NH_2$.

5. A compound according to claim 1 wherein $R^2$ is a mono-, di-, or trisubstituted 2-pyridinyl or 3-pyridinyl and the substituents are selected from the group consisting of
(a) hydrogen,
(b) halo,
(c) $C_{1-6}$alkoxy,
(d) $C_{1-6}$alkylthio,
(e) $C_{1-6}$alkyl,
(f) $CF_3$,
(g) CN.

6. A compound according to claim 1 wherein $R^1$ is $CH_3$ or $NH_2$, $R^2$ is a mono-, di-, or trisubstituted 2-pyridinyl or 3-pyridinyl and the substituents are selected from the group consisting of (a) hydrogen,
(b) halo,
(c) $C_{1-6}$alkoxy,
(d) $C_{1-6}$alkylthio,
(e) $C_{1-6}$alkyl,
(f) $CF_3$,
(g) CN.

7. A compound selected from the group consisting of
(a) 3-(4-(Methylsulfonyl)phenyl)-2-(3-pyridinyl)-2-cyclopenten-1-one,
(b) 2-(5-Chloropyridin-3-yl)-3-(4-(methylsulfonyl)phenyl)-2-cyclopenten-1-one,
(c) 2-(5-Bromo-3-pyridinyl)-3-(4-(methylsulfonyl)phenyl)-2-cyclopenten-1-one,
(d) 2-(2-Methyl-5-pyridinyl)-3-(4-(methylsulfonyl)phenyl)-2-cyclopenten-1-one,
(e) 2-(2-Methoxy-5-pyridinyl)-3-(4-(methylsulfonyl)phenyl)-2-cyclopenten-1-one,
(f) 2-(2-Pyridinyl)-3-(4-(methylsulfonyl)phenyl)-2-cyclopenten-1-one,
(g) 2-(5-Chloro-2-pyridinyl)-3-(4-(methylsulfonyl)phenyl)-2-cyclopenten-1-one,
(h) 2-(5-Bromo-2-pyridinyl)-3-(4-(methylsulfonyl)phenyl)-2-cyclopenten-1-one,
(i) 2-(4-Pyridinyl)-3-(4-(methylsulfonyl)phenyl)-2-cyclopenten-1-one, or a pharmaceutically acceptable salt thereof.

8. A compound according to claim 7 wherein the pharmaceutically acceptable salt is an acid salt of citric, hydrobromic, hydrochloric, maleic, methanesulfonic, phosphoric, sulfuric or tartaric acid.

9. A compound according to claim 8 wherein the pharmaceutically acceptable salt is an acid salt of hydrochloric or methanesulfonic acid.

10. A pharmaceutical composition for treating an inflammatory disease susceptible to treatment with an non-steroidal anti-inflammatory agent comprising: a non-toxic therapeutically effective amount of a compound according to claim 1 and a pharmaceutically acceptable carrier.

11. A pharmaceutical composition for treating cyclooxygenase mediated diseases advantageously treated by an active agent that selectively inhibits COX-2 in preference to COX-1 comprising: a non-toxic therapeutically effective amount of a compound according to claim 1 and a pharmaceutically acceptable carrier.

12. A method of treating an inflammatory disease susceptible to treatment with an non-steroidal anti-inflammatory agent comprising: administration to a patient in need of such treatment of a non-toxic therapeutically effective amount of a compound according to claim 1 and a pharmaceutically acceptable carrier.

13. A method of treating cyclooxygenase mediated diseases advantageously treated by an active agent that selectively inhibits COX-2 in preference to COX-1 comprising: administration to a patient in need of such treatment of a non-toxic therapeutically effective amount of a compound according to claim 1.

* * * * *